United States Patent [19]
Katsurada

[11] Patent Number: 5,239,983
[45] Date of Patent: Aug. 31, 1993

[54] CONNECTOR APPARATUS FOR ENDOSCOPE

[75] Inventor: Hiroyuki Katsurada, Tokyo, Japan

[73] Assignee: Asahi Kogaku Kogyo Kabushiki Kaisha, Tokyo, Japan

[21] Appl. No.: 757,286

[22] Filed: Sep. 10, 1991

[30] Foreign Application Priority Data

Sep. 18, 1990 [JP] Japan .................. 2-248052

[51] Int. Cl.$^5$ .................. A61B 1/06; H01R 33/945
[52] U.S. Cl. .................. 128/6; 439/577; 439/909
[58] Field of Search .................. 128/6, 4, 11, 13, 16, 128/18, 22; 358/98; 439/218, 222, 247, 284, 638–640, 166–174, 190–191, 502, 4, 34, 35, 909, 577; 350/96.2, 96.26; 359/54, 53; 385/117, 118

[56] References Cited

U.S. PATENT DOCUMENTS

| 4,416,268 | 11/1983 | Hagino | 128/6 |
| 4,767,181 | 8/1988 | McEowen | 439/577 |
| 4,888,639 | 12/1989 | Yabe et al. | 358/98 |
| 4,919,621 | 4/1990 | Ams | 439/191 |
| 5,036,834 | 8/1991 | Sugiyama et al. | |

FOREIGN PATENT DOCUMENTS

| 57-37435 | 3/1982 | Japan . |
| 59-15017 | 1/1984 | Japan . |
| 61-133919 | 6/1986 | Japan . |
| 63-60117 | 4/1988 | Japan . |
| 1-25834 | 1/1989 | Japan . |
| 1-197714 | 8/1989 | Japan . |
| 1-174876 | 12/1989 | Japan . |
| 2-209124 | 8/1990 | Japan . |

OTHER PUBLICATIONS

English Language Abstract of JP Patent 57-37435.
English Language Abstract of JP Patent 61-133919.
English Language Abstract of JP Patent 59-15017.
English Language Abstract of JP Patent 63-60117.
English Language Abstract of JP Patent 1-25834.
English Language Abstract of JP Patent 1-197714.
English Language Abstract of JP Patent 1-174876.
English Language Abstract of JP Patent 2-209124.

*Primary Examiner*—Richard J. Apley
*Assistant Examiner*—John P. Leubecker
*Attorney, Agent, or Firm*—Sandler Greenblum & Bernstein

[57] ABSTRACT

A connector apparatus for an endoscope comprising a light guide connector for connecting an incident end of a light guide fiber bundle to a light source apparatus. An electrical connector is removably attached to the light guide connector to provide electrical connection with an external device. A flexible cable is connected at one end thereof to the electric connector and at the other end thereof to the light guide connector.

11 Claims, 6 Drawing Sheets

CONNECTOR APPARATUS FOR ENDOSCOPE

BACKGROUND OF THE INVENTION

The present disclosure relates to subject matter contained in Japanese Patent application No. 2-248052 (filed on Sep. 18, 1990), which is expressly incorporated herein by reference in its entirety.

FIELD OF THE INVENTION

The present invention relates to a connector apparatus for an endoscope, in which an electric connector, that is electrically connected to an external device, is disposed on a light guide connector for connecting the incident end of a light guide fiber bundle to a light source apparatus.

DESCRIPTION OF THE PRIOR ART

In a typical endoscope, light for illuminating an object is supplied from a light source apparatus through a light guide fiber bundle extending through the endoscope. To connect the incident end of the light guide fiber bundle to the light source apparatus, a connector (light guide connector) is provided at an end of a flexible connecting tube.

In the case of a video endoscope which is designed to transmit an observed image electrically by use of a solid-state imaging device, an external device (video processor) is needed to drive the solid-state imaging device and process the image signal. It is therefore necessary to connect an electric circuit in the endoscope to the video processor. In one type of conventional connector apparatus, as shown exemplary in FIG. 6, an electric connector 82 is formed on one side surface of a light guide connector 81. A video processor 86 is connected to the electric connector 82 through a cable 85 having connectors 83 and 84 attached to both ends thereof. Reference numerals 87 and 88 denote a light source apparatus and a monitor, respectively.

With the recent spread of video endoscopes, the need of making their peripheral equipment even more convenient has been increasing. A light source apparatus with a video processor incorporated therein, i.e., a light source-processor integral unit, has recently been developed.

However, if a conventional connector apparatus of the type described above is used in a video endoscope, a light source-processor integral unit 90 needs to be formed with a light guide connector receptacle 91 for receiving the light guide connector 81, and an electric connector receptacle 92 for receiving the electric connector 84 separately, as shown in FIG. 7.

For this reason, the production cost rises, and the user needs to connect the two pairs of connector members separately when the connector apparatus is connected to the light source-processor integral unit 90. In addition, the light source-processor integral unit 90 itself increases in size. Previously, it has been impossible to assemble the light source apparatus and the video processor into one unit.

SUMMARY OF THE INVENTION

An object of the present invention is to provide a connector apparatus for an endoscope which can be readily connected to an external device and a light source apparatus, which are separate from each other, and which enables an external device, integrated with a light source as one unit, to be conveniently used in a compact form.

According to the present invention, there is provided a connector apparatus for an endoscope comprising: a light guide connector for connecting an incident end of a light guide fiber bundle to a light source apparatus; an electric connector removably attached to the light guide connector to provide electrical connection with an external device; and a flexible cable connected at one end thereof to the electric connector and at the other end thereof to the light guide connector.

Other objects and advantages of the present invention will become apparent from the following detailed description of illustrated embodiments of the invention.

BRIEF DESCRIPTION OF THE DRAWINGS

The present invention may be more fully understood from the description of preferred embodiments of the invention set forth below, together with the accompanying drawings, in which.

DESCRIPTION OF THE EMBODIMENTS

Figure 1:
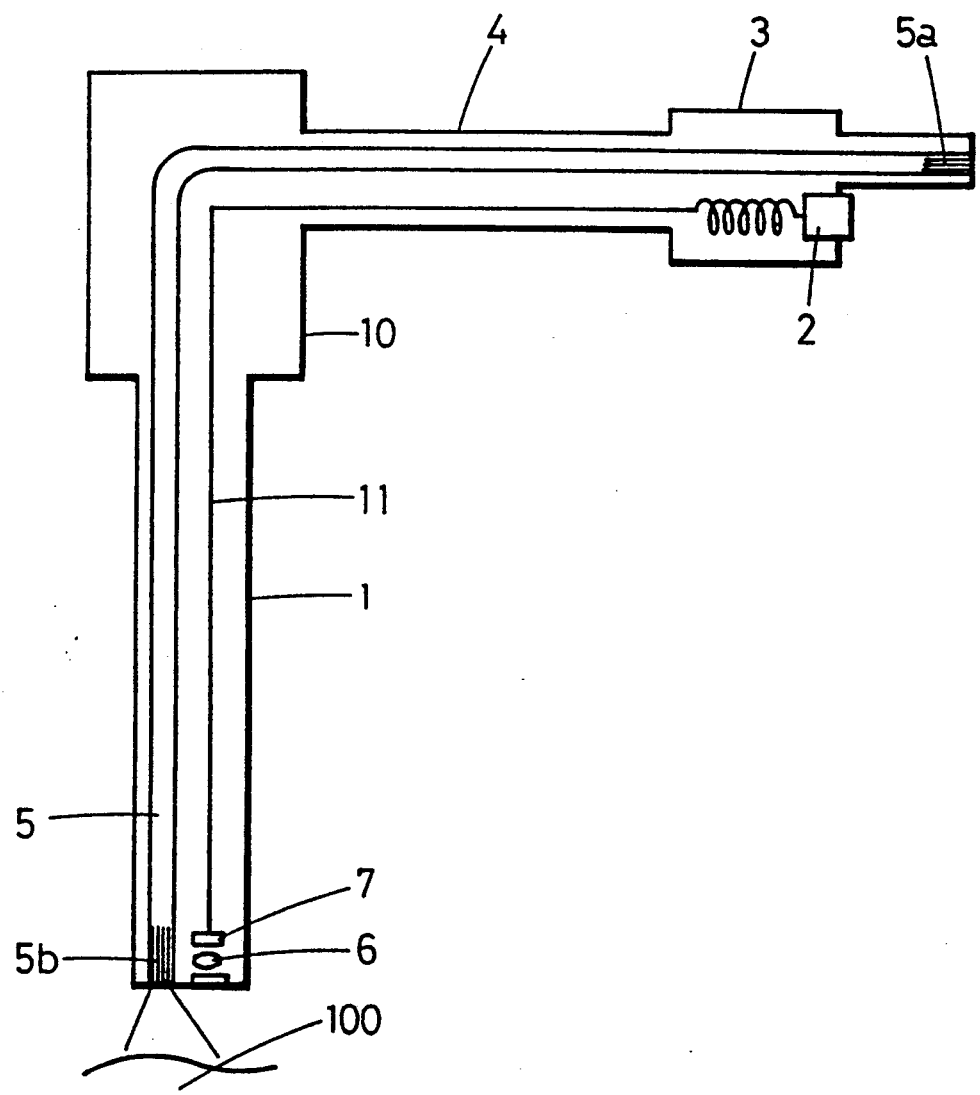
FIG. 1 is a schematic view of a video endoscope according to one embodiment of the present invention.

Referring to FIG. 1, which is a schematic view of a video endoscope, reference numeral 1 denotes a flexible insert part which is inserted into a hollow organ in the patient's body. There is also provided a control part 10 and a light guide connector 3 that are connected to a light source apparatus. A flexible connecting tube 4 connects together the light guide connector 3 and the control part 10.

A light guide fiber bundle 5, for illuminating an object 100, has an incident end 5a disposed in the light connector 3, and an emergent end 5b disposed in the distal end portion of the insert part 1.

In addition, an objective optical system 6 is disposed in the distal end portion of the insert part 1. A solid-state imaging device 7, for example, a CCD (Charge-Coupled Device), is disposed at the imagery position of the objective optical system 6 to convert an observed image into an electric signal and transmit it. An electric connector 2, for connection with an external video processor, is connected to the solid-state imaging device 7 through a cable 11, and removably attached to the light guide connector 3.

Figure 2:
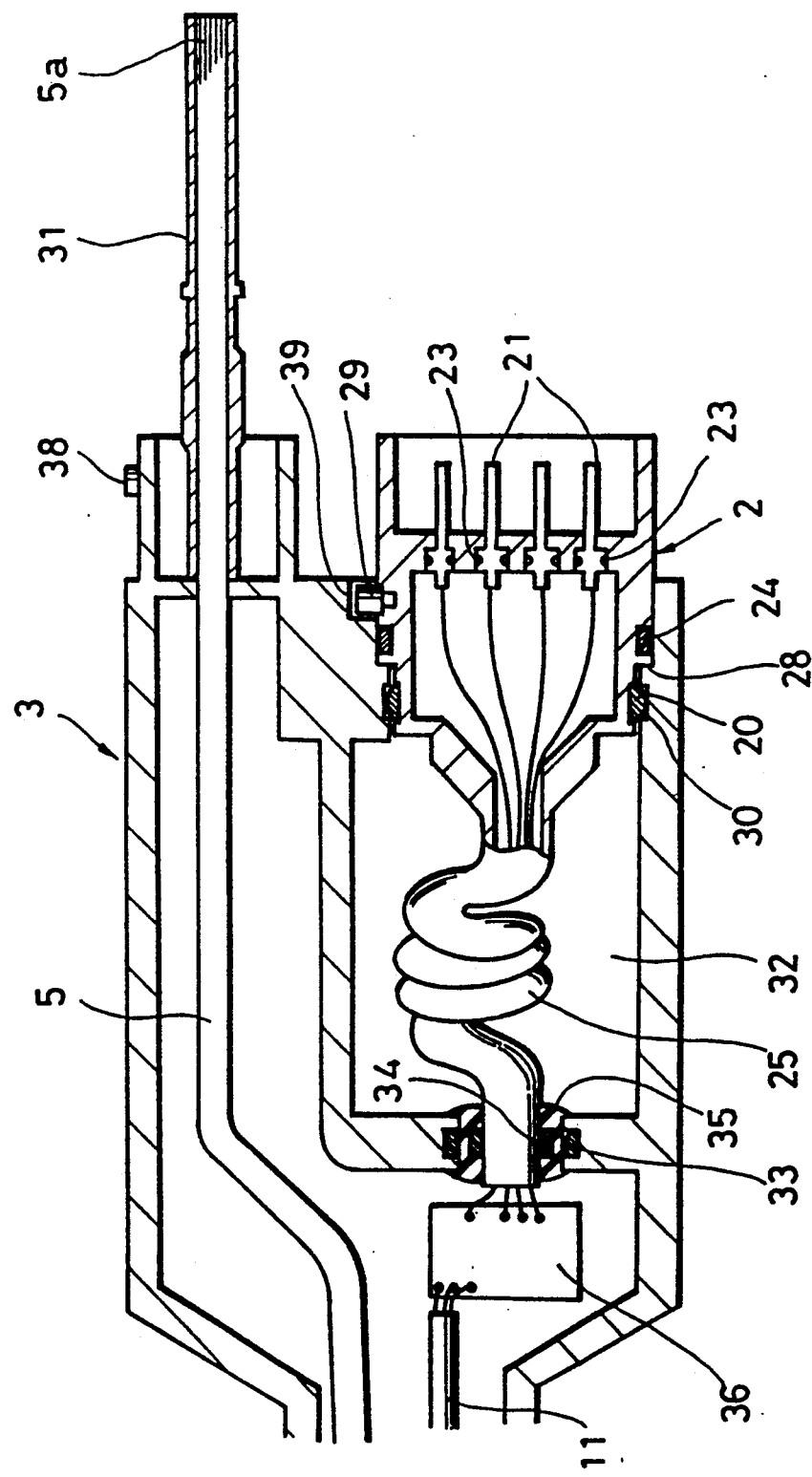
FIG. 2 is a sectional side view of a connector apparatus according to the embodiment.

FIG. 2 shows the light guide connector 3 and the electric connector 2.

The light guide fiber bundle 5 extends through an elongate connecting tube 31, projecting from the end of the light guide connector 3. The incident end 5a of the light guide fiber bundle 5 is exposed at the projecting end of the connecting tube 31.

The electric connector 2 is removably attached to the end portion of the light guide connector 3. More specifically, the electric connector 2 is removably inserted into a receiving bore provided in the end face of the light guide connector 3, until it abuts against a stopper portion 28.

The electric connector 2 has a spring metal, C-ring 20 fitted in a groove provided in the outer peripheral portion thereof. The C-ring 20 engages with a groove 30 formed in the light guide connector 3, thereby clicking the two connectors 2 and 3 into connection with each other. Accordingly, it is necessary, in order to disconnect the connectors 2 and 3, to pull out the electric connector 2 from the light guide connector 3 with a force greater than a predetermined level.

When the electric connector 2 is in connection with the light guide connector 3, contact pins 21 of the electric connector 2 face in the same direction as that in which the connecting tube 31 extends, so that the two connectors 2 and 3 can be connected to respective mating members in one connecting operation.

A positioning pin 29, which is provided on the outer peripheral portion of the electric connector 2, is engaged with a groove 39 provided in the light guide connector 3, to place the two connectors 2 and 3 in a predetermined positional relationship with each other.

Each contact pin 21 has a sealing O-ring 23, attached to the root portion thereof to prevent water or other foreign matter from entering the electric connector 2.

Similarly, a sealing O-ring 24 is attached to the outer peripheral portion of the electric connector 2, to prevent water or other foreign matter from entering the light guide connector 3 when the electric connector 2 is in connection with the light guide connector 3.

A flexible cable 25, which comprises a bundle of lead wires connected respectively to the contact pins 21, is spirally accommodated in a cable accommodating chamber 32 defined in the light guide connector 3.

A bushing 35 is attached to a bore provided in the wall portion of the cable accommodating chamber 32 to pass the cable 25 therethrough. The bushing 35 has sealing O-rings 33 and 34 fitted in the outer and inner peripheries thereof. Accordingly, even when the electric connector 2 is not connected with the light guide connector 3, water or other foreign matter is prevented from entering beyond the cable accommodating chamber 32.

A printed board 36 is formed with a drive circuit for the solid-state imaging device 7. The above-described two cables 11 and 25 are connected to input and output terminals of the printed board 36.

A positioning pin 38 serves to position the light guide connector 3 when connected to a light source apparatus.

Figure 3:
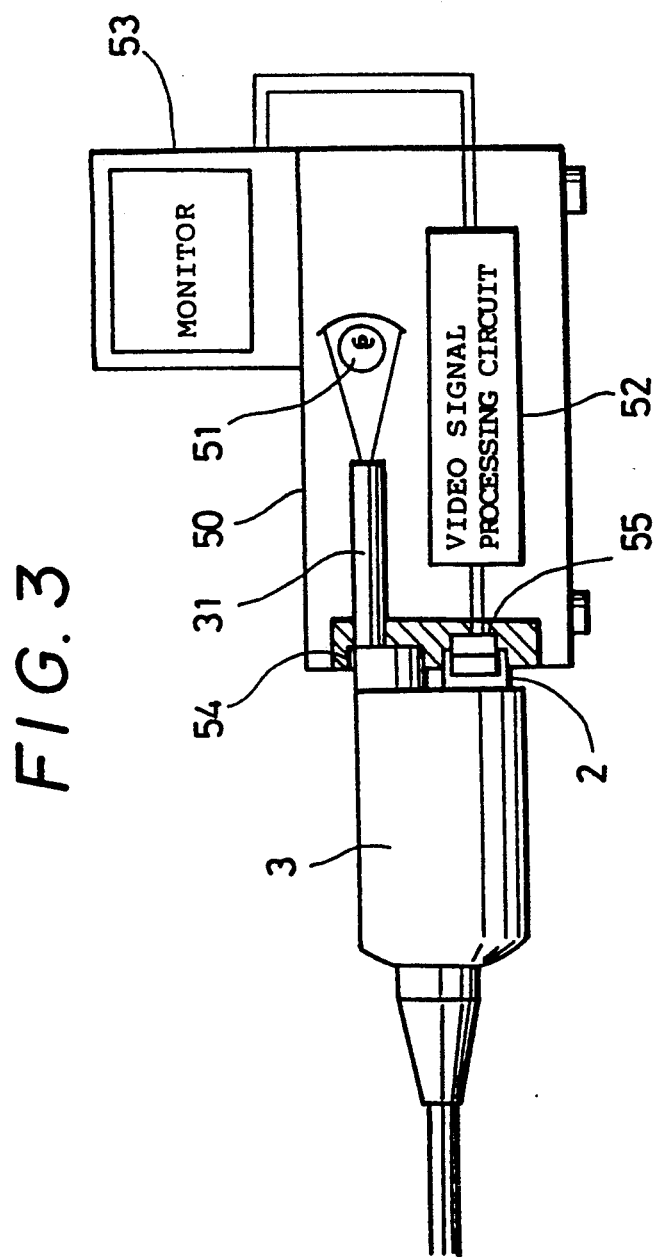
FIG. 3 is a schematic view of the connector apparatus that is connected to a light source-processor integral unit.

FIG. 3 shows the connector apparatus of this embodiment which is connected to a light source-processor integral unit 50. Reference numerals 51, 52 and 53 denote a light source lamp, a video signal processing circuit and a monitor, respectively.

The light source-processor integral unit 50, to which is connected a connector apparatus for an endoscope such as that shown in FIG. 2, has a light guide connector receptacle 54 which receives the light guide connector 3, and an electric connector receptacle 55 which receives the electric connector 2. These two connector receptacles 54 and 55 can be formed in an integral structure.

Accordingly, the connection of the light guide connector 3 and the connection of the electric connector 2 can be effected in one operation. In addition, the space occupied by the connector receptacles 54 and 55 of the light source-processor integral unit 50 can be reduced by a large margin.

Upon completion of the connection of the two connectors 2 and 3 in this way, illuminating light is supplied to the light guide fiber bundle 5 from the light source lamp 51. A signal transfer is carried out between the solid-state imaging device 7 and the video signal processing circuit 52 through the contact pins 21, so that an image of the object 100, formed on the solid-state imaging device 7, is displayed on the monitor 53.

Figure 4:
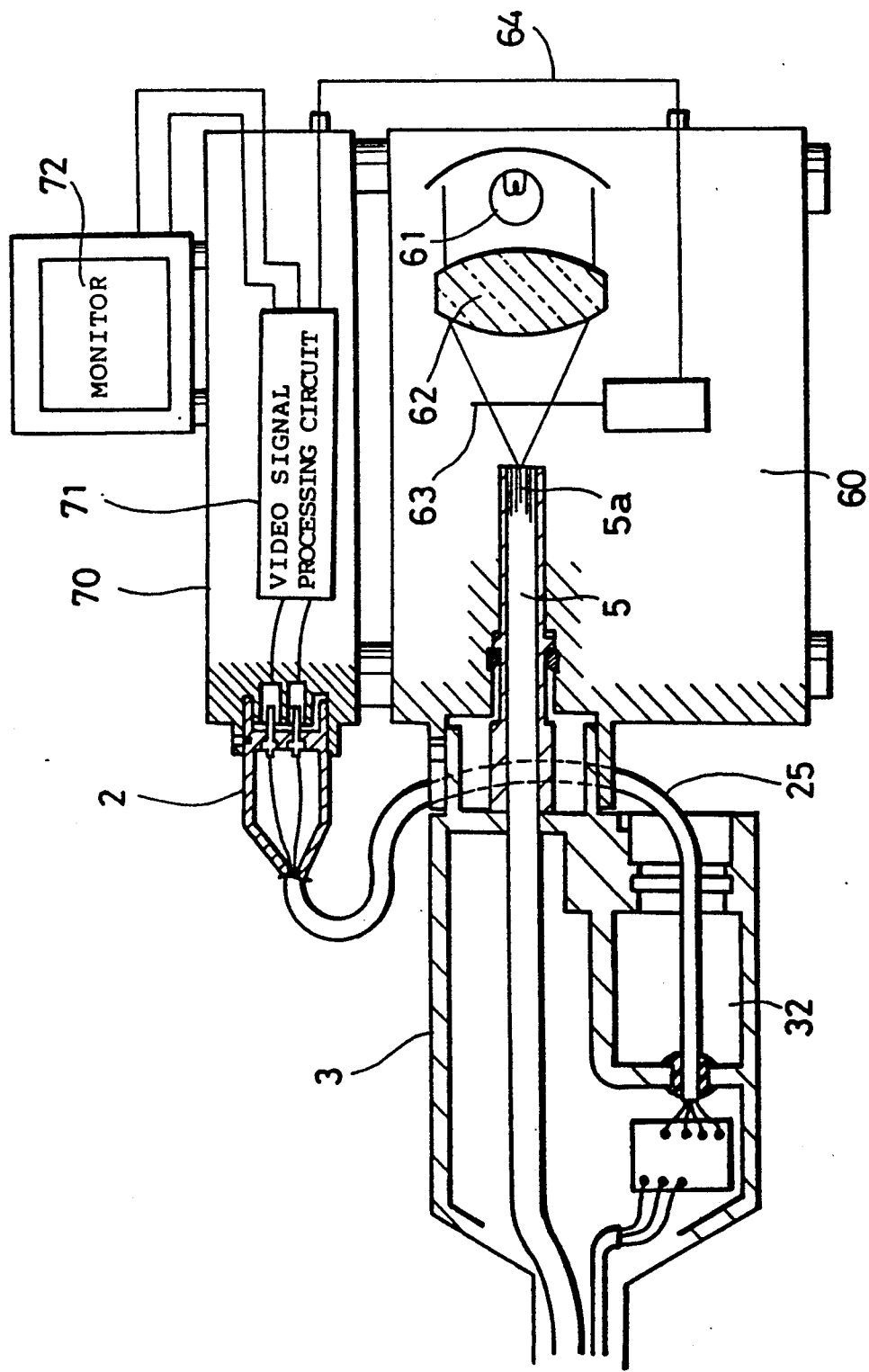
FIG. 4 is a schematic view of the connector apparatus that is connected to both a light source apparatus and a processor, which are discrete units.

FIG. 4 shows the connector apparatus of this embodiment that is connected to a light source apparatus 60 and a video processor 70, which are discrete units. A light source lamp 61, condenser lens 62, and variable diaphragm 63 are used to control the brightness level of illuminating light made incident on the light guide fiber bundle 5.

The operation of the variable diaphragm 63 is controlled in response to a control signal which is input thereto from the video processor 70 via a connecting cable 64.

Reference numeral 71 denotes a video signal processing circuit provided in the video processor 70 and monitor 72.

When the connector apparatus of this embodiment is to be connected to both the light source apparatus 60 and the video processor 70, which are discrete units, the electric connector 2 is detached from the light guide connector 3 and the cable 25 is extended from the cable accommodating chamber 32, as shown in FIG. 4. By so doing, the light guide connector 3 can be connected to the light source apparatus 60, while the electric connector 2 can be connected to the video processor 70.

Figure 5:
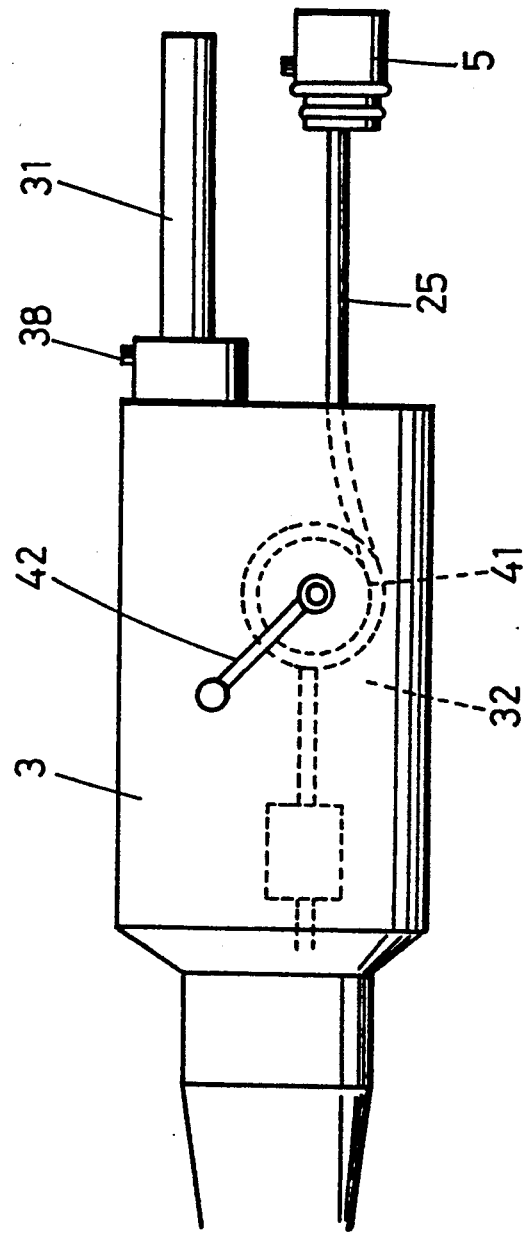
FIG. 5 is a side view of a connector apparatus according to another embodiment of the present invention.
Figure 6:
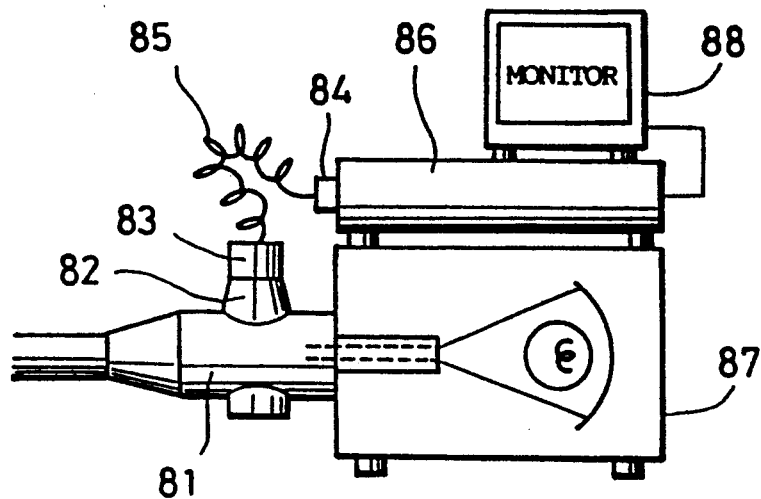
FIGS. 6 and 7 illustrate a conventional connector apparatus for an endoscope.
Figure 7:
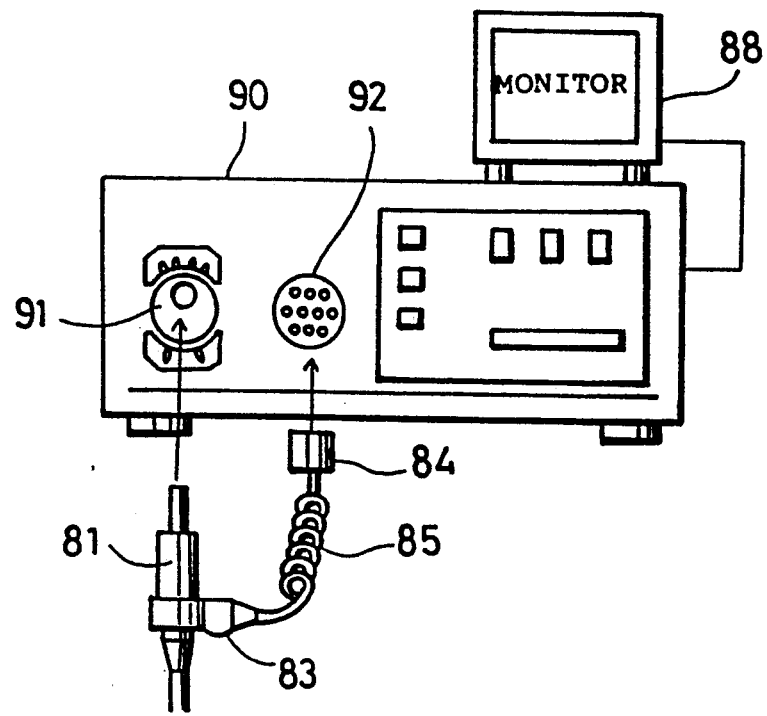

FIG. 5 shows another embodiment of the present invention, in which a reel 41, for taking up the cable 25, is rotatably provided in the cable accommodating chamber 32 in the light guide connector 3, so that the cable 25 can be taken up onto the reel 4 by rotating it with a handle 42, that is provided outside the light guide connector 3. The rest of the arrangement is the same as that of the embodiment shown in FIG. 2.

By virtue of the above arrangement, the fear of disconnection of the cable 25 is minimized, and the cable accommodating chamber 32 can be reduced in size.

According to the present invention, when the connector apparatus is to be connected to an external device which is assembled together with a light source apparatus as one integral unit, the electric connector is attached to the light guide connector, thereby enabling the two connectors to be connected simultaneously. When the connector apparatus is to be connected to an external device which is separate from a light source, the electric connector is detached from the light guide connector, thereby enabling the two connectors to be connected separately from each other.

Accordingly, the connector apparatus can be readily connected to an external device which is separate from a light source apparatus, and it can be readily connected in one operation to both an external device and a light source apparatus, which are assembled together as one integral unit. In addition, a light guide connector receptacle and electric connector receptacle of such an integral external unit can be formed in a compact integral structure. Therefore, it is possible to achieve a reduction in size of such an external device integrated with a light source.

While the invention has been described by reference to specific embodiments chosen for purposes of illustration, it should be apparent that numerous modifications could be made thereto by those skilled in the art without departing from the basic concept and scope of the invention. For example, the electric connector may provide connection for not the signal from the solid-state imaging device but an exposure control signal for photography.

I claim:

1. A connector apparatus for an endoscope comprising:
   a light guide connector for connecting an incident end of a light guide fiber bundle to a light source apparatus, said light guide connector facing in a first direction;
   an electric connector releasably secured within said light guide connector, and positioned to face in said first direction, whereby said electric connector is adapted to provide electrical connection with an external device; and
   a flexible cable being fixedly connected at one end thereof to said electric connector and at an other end thereof being fixedly connected to said light guide connector.

2. A connector apparatus for an endoscope according to claim 1, said light guide connector further comprising means for accommodating said flexible cable, wherein, when said electric connector is attached to said light guide connector, said flexible cable is accommodated in said light guide connector, whereas, when said electric connector is detached from said light guide connector, said flexible cable can be extended from said light guide connector.

3. A connector apparatus for an endoscope according to claim 1, wherein said electric connector is attached to said light guide connector and positioned to face in a same direction as the incident end face of said light guide fiber bundle.

4. A connector apparatus for an endoscope according to claim 1, further comprising positioning means for placing said electric connector and said light guide connector in a predetermined positional relationship with each other when said electric connector is attached to said light guide connector.

5. A connector apparatus for an endoscope according to claim 1, wherein said electric connector is provided with a plurality of contact pins, said flexible cable comprising a bundle of lead wires connected respectively to said contact pins.

6. A connector apparatus for an endoscope according to claim 2, wherein said means for accommodating comprises a chamber for accommodating said flexible cable.

7. A connector apparatus for an endoscope according to claim 6, wherein said flexible cable accommodating chamber has a reel rotatably provided therein to take up said cable, said reel being rotated with a handle provided outside said light guide connector, thereby enabling said cable to be taken up onto said reel.

8. A connector apparatus according to claim 1 in combination with an endoscope, wherein said endoscope has a light guide fiber bundle, and a solid state imaging device provided at the distal end of an insert part thereof to convert an observed image into an electric signal and to transmit said signal, said endoscope further including an external device, wherein said electric signal is transmitted to said external device from said solid state imaging device through said electrical connector.

9. A connector apparatus for an endoscope according to claim 8, wherein the external device is provided as an integral part of the light source apparatus, so that said electric connector is connected to the external device in a state where it is secured to said light guide connector.

10. A connector apparatus for an endoscope according to claim 8, wherein the external device is separate from the light source apparatus, so that said electric connector is connected to the external device in a state where it is detached from said light guide connector.

11. A connector apparatus for an endoscope comprising:
    a light guide connector for connecting an incident end of a light guide fiber bundle to a light source apparatus; and
    an electric connector adapted for providing electrical connection with an external device, a flexible cable being connected at one end thereof to said electric connector and at an other end thereof to said light guide connector, said electric connector being provided on said light guide connector so as to be movable between first and second operable positions, said first position being near a portion of said light guide connector that is connected to the light source apparatus, and at which said electric connector is releasably secured to said light guide connector to extend in the same direction as that in which said light guide connector is connected to the light source apparatus, and said second position being more remote from said portion of said light guide connector than said first position.

* * * * *

UNITED STATES PATENT AND TRADEMARK OFFICE
CERTIFICATE OF CORRECTION

PATENT NO. : 5,239,983
DATED : August 31, 1993
INVENTOR(S) : Hiroyuki KATSURADA

It is certified that error appears in the above-indentified patent and that said Letters Patent is hereby corrected as shown below:

On the cover, in section [57], "ABSTRACT", line 3, change "alight" to ---a light---.

Signed and Sealed this

Twenty-second Day of August, 1995

Attest:

BRUCE LEHMAN

Attesting Officer     Commissioner of Patents and Trademarks